United States Patent [19]

Swon et al.

[11] Patent Number: 4,855,821

[45] Date of Patent: · Aug. 8, 1989

[54] VIDEO TIMING DEVICE FOR PHARMACEUTICAL TABLET TESTING

[76] Inventors: James E. Swon, 12 Brookside, Brookside, N.J. 07926; Henry Hofer, 8 Telemark Rd., Rockaway, N.J. 07866

[21] Appl. No.: 156,032

[22] Filed: Feb. 16, 1988

[51] Int. Cl.⁴ .................... H04N 7/18; G01N 19/00
[52] U.S. Cl. ..................................... 358/101; 73/866; 358/93
[58] Field of Search .............. 358/93, 101, 108; 73/866

[56] References Cited

U.S. PATENT DOCUMENTS

| | | | |
|---|---|---|---|
| 3,618,395 | 11/1971 | Melliger | 73/866 |
| 3,791,222 | 2/1974 | Goodhart | 73/866 |
| 4,279,860 | 7/1981 | Smolen | 73/866 |
| 4,413,277 | 11/1983 | Murray | 358/101 |
| 4,472,960 | 9/1984 | Motoyama | 73/866 |
| 4,514,758 | 4/1985 | Berthel | 358/108 |
| 4,636,849 | 1/1987 | Wada | 358/101 |
| 4,681,858 | 7/1987 | Chaudhari | 73/866 |
| 4,754,657 | 7/1988 | Schneider | 73/866 |

*Primary Examiner*—Howard W. Britton
*Attorney, Agent, or Firm*—William T. Hough

[57] ABSTRACT

A combination for observing and recording required periods of time for dissolution and/or disintegration of pharmaceutical solid dosage forms such as tablets, including one or more, preferably two electronic video camera lense mechanisms positioned at different locations of surveillance of a plurality of different separate tablet-containing vessels each separately supporting different tablet(s) of camera-lens support structure anchored onto a vessel (waterbath) containing the liquid media, the tablet-containing vessels being moved alternately upwardly and downwardly and/or revolvably, with a time recorder recording intermittently or continuously exact times of surveillance testing of tablets, and a monitor for playing-back on a single or preferably divided-screen recorded observations and recorded times associated therewith.

19 Claims, 2 Drawing Sheets

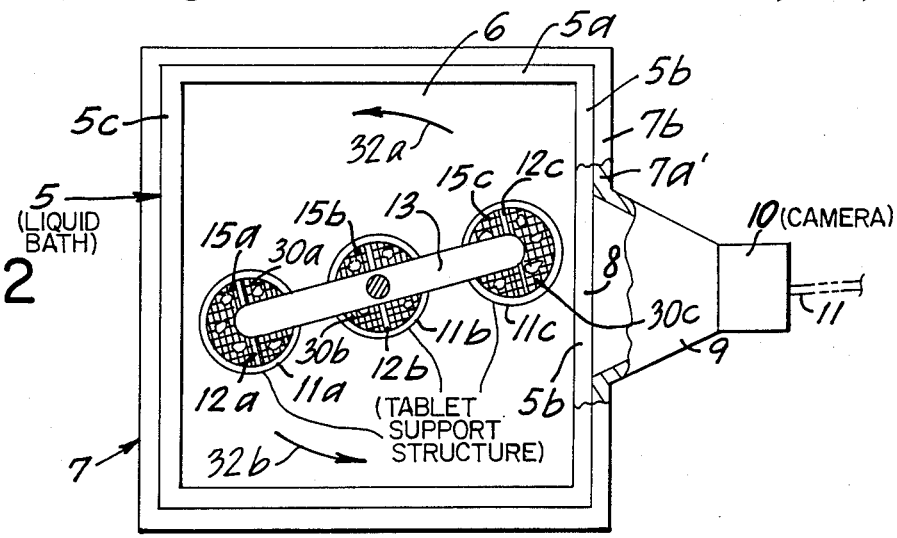
FIG. 2
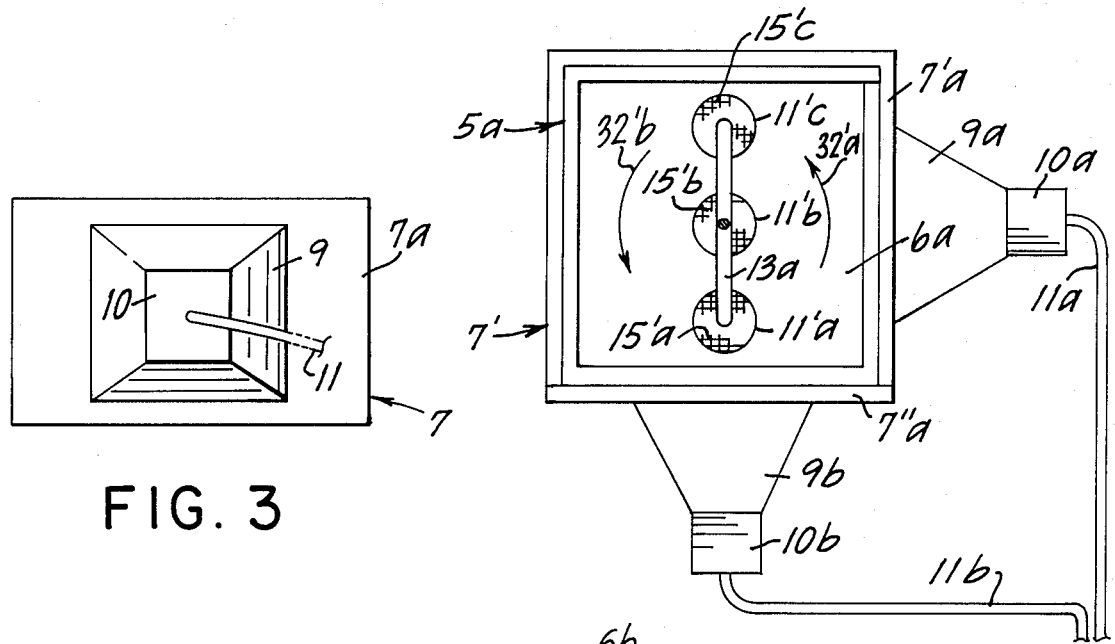
FIG. 3
FIG. 4
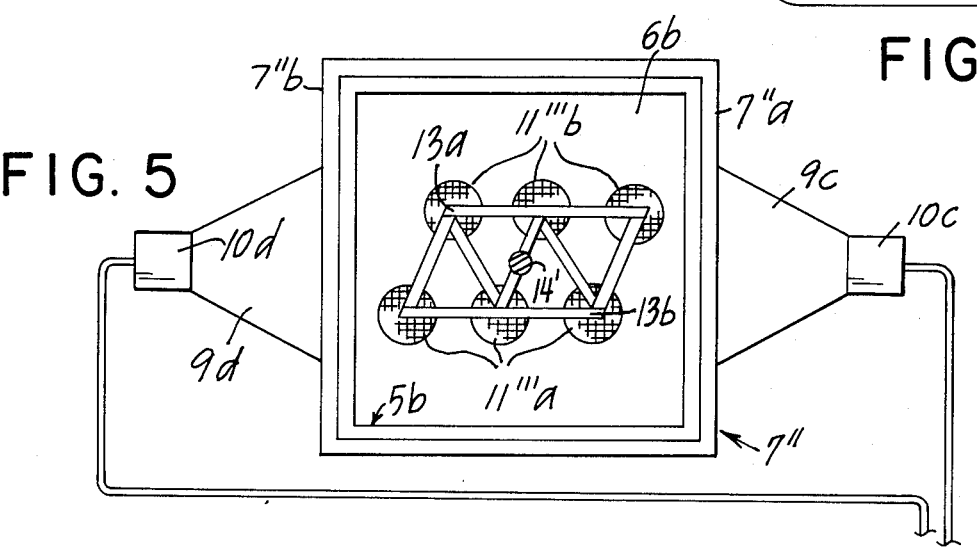
FIG. 5

VIDEO TIMING DEVICE FOR PHARMACEUTICAL TABLET TESTING

This invention is directed to a video device for recording disintegration and/or dissolving times of pharmaceutically tested tablets or capsules individually or preferably simultaneously tested in separate holders within a common liquid media.

BACKGROUND TO THE INVENTION

Prior to the present invention, there have existed mechanical structures and vessels for the simultaneous testing of separately supported pharmaceutical tablets tested for rate or required times of disintegration or for time of dissolution in liquid media such as water, as supporting vessels are moved therethrough. Required times are recorded as observed by a worker who intermittently checks the progress—noting that some disintegrations require extended times, sometimes hours, rather than a mere few minutes. Not only does such procedure tie-down valuable workers needed for and normally assigned to other duties concurrently, but the mere fact that such observations are intermittent at best, the recorded times and observations are most likely highly unreliable and inexact, as to true times of actual disintegration.

For testing disintegration rate, the prior art test is provided to determine federal compliance with the limits on disintegration stated in the individual monographs except and where the label states that the tablets or capsules are intended for use as troches, or are to be chewed, or are designed to liberate the drug content gradually over a period of time or to release the drug over two or more separate periods with a distinct time interval between such release periods. The type of units under test is determined from the labeling and from observation, and the appropriate prior art procedure is applied to six or more dosage units.

For disintegration purposes for this type test(s), disintegration does not imply complete solution of the unit or even of its active constituent. Complete disintegration is defined as that stat in which any residue of the unit, except fragments of insoluble coating or capsule shell, remain on the screen of the test tablet-support apparatus in a soft mass having no palpably firm core.

A typical prior art apparatus for testing disintegration time(s) consists of a basket-rack assembly, a 1000 ml. low-form beaker for the immersion fluid, a thermostatic arrangement for heating the fluid between 35 and 39 degrees, i.e. about 37.5 degrees, Centigrade and a device for raising and lowering the basket in the immersion fluid at a constant frequency rate between 29 and 32 cycles per minute through a distance of not less than 5.3 cm. and not more than 5.7 cm.. The volume of the fluid in the vessel is such that at the highest point of the upward stroke the wire mesh (that supports the tablet(s) remains at least 2.5 cm below the surface of the fluid and descends to not less than 2.5 cm. from the bottom of the vessel on the downward stroke. The time required during the upward stroke is equal to the time required for the downward stroke, and the change in stroke direction is a smooth transition rather than an abrupt reversal motion. The basket-rack(s) support-assembly(ies) move substantially vertically along its(their) vertical axis-(axes). There is no appreciable horizontal motion or movement of the axis from the vertical.

For the disintegration assembly, the basket rack assembly of the prior art typically consists of six open-ended glass tubes, each 7.75 cm. (plus or minus 0.24 cm.) in length and having an inside diameter of approximately 21.5 mm and a wall approximately 2 mm. thickness. The tubes are held in a vertical position by two plastic plates, each about 9 cm in diameter and 6 mm. in thickness, with six holes, each about 24 mm. in diameter, equidistant from the center of the plate and equally spaced from one another. Attached to the under surface of the lower plate is a 10-mesh (typically) No. 23 (0.025 inch) W. and M. gauge woven stainless steel wire cloth having typically a plain square weave. The prior art parts of the apparatus are assembled and are rigidly held by bolts passing through two plastic plates with suitable mechanical mechanism being provided to suspend the basket-rack assembly from the raising and lowering device.

For disintegration procedure with the above-noted mechanical mechanism, there are separate procedures followed for each of different types of tablets, such as for uncoated tablets, and plain coated tablets, and for enteric-coated tablets, and for buccal tablets, and for sublingual tablets, and the like. It is not a purpose nor function of the present invention described hereinafter to distinguish between nor alter such procedures.

For disintegration, a typical prior art disintegration tester is the Vanderkamp Tablet Disintegration Tester of VAN-KEL Industries, Inc., having a machine for alternately raising and lowering the basket(s), and including one power base with a single basket hanger, a basket-rack assembly, a set of six fluted plastic discs, a basket suspension rod, and disintegration beakers. A complete system includes a disintegration tester, a basket hanger, one or more racket assemblies, fluted plastic discs, basket suspension rods, and disintegration beakers. A six-basket system would include 6 basket capacity tester, six unit basket hanger, six basket rack assemblies, six sets of six fluted plastic discs, six basket suspension rods, and six disintegration beakers. These details are given for purposes of providing common knowlege and understanding of the state of the prior art. In this same context, there are available prior art water baths of clear acrylic or stainless steel typically ranging from 18 to 42 inches long, and typically twelve inches wide and eight inches deep. There are also available precision baths of typically square width-length dimensions. It is common for such various baths or liquid-vessels to include mechanisms and electrical wiring or circuitry as to provide temperature at temperatures that may be manually set or reset and/or maintained, and mechanisms for keeping the water stirred or circulated to assure constant temperature(s) throughout the liquid within the bath-vessel(s).

With regard to dissolution testing, a typical prior art tester is the Vanderkamp [registered trademark] 600 tester of VAN KEL Industries, Inc. in which several different groups of tablets are separately contained in separate support structures within a common liquid media of a common transparent waterbath(vessel), with a separate paddle provided and inserted from above, for each separately supported(contained) tablets—each one or more separately supported(contained) tablets being supported(contained) within typically an open-top transparent vessel having a rounded bottom. The above-noted typical prior art dissolution tester for an all six-spindle tester, includes one Vanderkamp (trademark) 600 including complete drive unit with four post assembly and flask covers, and six rotating basket assemblies [of USP Method (T-1045029)] or stainless steel teflon coated paddles [of USP Method II (T-1045-7037), and six 1000 ml. round bottom glass dissolution vessel (K-1010) or plastic dissolution vessels (K-1012), and one transparent waterbath of typically ⅜ inch acrylic, and one set of stainless steel locating gauges. A typical external bath circular model is available as an acrylic waterbath with circulator and tygon tubing. There is also alternately available such bath that is a "mounted" circular model having an acrylic waterbath with a circulator and a mounting frame. In these models, the circulating paddles and/or supports of the separate vessels, may individually or as a group be intermittently raised or lowered into or from the liquid media contained in the bath vessel. These dissolution baths likewise have associated therewith temperature sensors and mechanism for heating or maintaining temperature of the bath's liquid at temperature(s) that may be manually set.

With the prior art hardware and procedures above-noted, there have existed problems relating to both time requirements of workers to maintain constant observations monitoring of progressive disintegration(s) and/or dissolution(s) of set(s) of tablets, and questionable and/or unreliable results as reported that result from unreliable intermittent observation(s) made by observers making the occasional intermittent observation from time to time over sometimes a running period of many hours.

It is also a fact that casual personal observations are not always exact nor precise nor reliable in actual practice, and yet heretofore there has not existed any corrective hardware making possible more exact and reliable data. The task heretofore has been further complicated because of the fact of moving supports(containers) and/or baskets and/or paddles, associated with the tablets, by which exact observation is hampered.

OBJECTS

Objects of the present invention include the overcoming and/or avoiding of problems and difficulties of the types described above.

Other objects include the obtaining of a novel device by which reliable surveillance is made possible and is recorded for subsequent careful review and study.

Other objects include the perfection of such device suitable for each and/or both the procedures required for disintegration and/or dissolution of tablets, in the testing thereof.

Other objects become apparent from the preceding and following disclosure.

Preceding objects above-noted are obtained by the invention described herein.

SUMMARY OF THE INVENTION

The invention includes a surveillance device advantageously for recording pharmaceutical surveillance and recording timing rates of disintegration or of dissolving of pharmaceutical tablets, as follows.

The broad combination includes: (a) one or more electronic video camera mechanism(s) adapted for powering movement of and for surveillance of tablets undergoing disintegration or dissolution of tablets in liquid media, such as typically water; (b) a camera support mechanism and/or structure adapted to support and position the electronic camera mechanism, such that the camera means may observe tablets being disintegrated or dissolved in the liquid media; (c) a timing mechanism and structure thereof, adapted to indicate running and/or intermittent times during surveillance of the camera mechanism; and (d) video recording mechanism and structure thereof, adapted to record observations made by said camera mechanism and to record the times associated with the camera observation during the powering and surveillance by the camera mechanism.

In a preferred embodiment, there is additionally included: (e) a tablet support and movement mechanism and structure thereof, adapted for moving supported tablet(s) within the liquid media, sufficiently to cause the tablet(s) to disintegrate and/or to dissolve over a period of time; and (f) a vessel mechanism and structure thereof adapted to contain and retain liquid media such as typically water, and adapted to receive supported tablet(s) and the supporting structure therefor, sufficiently into the liquid media as to make possible the disintegration and/or dissolving of tablet(s) moved by the tablet support mechanism.

In a further preferred embodiment, the tablet support mechanism and structure includes a plurality of separate compartments adapted to provide for segregating a plurality of at-least two or more tablets from one or more segregated other tablets while the plurality of compartments are being moved within the liquid media. The tablet support mechanism and structure thereof may be further adapted such that the tablet support mechanism and structure thereof further is adapted for plurality of separate compartments to be positioned relative to the camera mechanism and structure thereof to make the plurality substantially concurrently susceptible to surveillance by the camera(s).

In a further preferred embodiment, the plurality of compartments are arranged such that all compartments are at-least partially viewable by a single camera. In a further preferred arrangement, the plurality of compartments are arranged in off-set rows such that a forward side face of one row of compartments is substantially totally visible to a camera while remaining others of the compartments is at-least partially visible concurrently. In an alternate preferred embodiment, the plurality are arranged in a straight-line side-by-side serial arrangement.

In a further preferred embodiment, the tablet support mechanism and structure thereof, includes a mechanism for moving one or more of the plurality of compartments to and from alternate locations and positions at which intermittently one or more thereof is susceptible of surveillance by one or more of the camera(s) of this invention above-described.

In a further preferred embodiment, the tablet and support means and structure thereof is adapted optionally to also revolve the plurality of compartments in one direction or the other, or intermittently in alternate directions. Upward and downward alternate movement(s) noted-above may be separately or concurrently initiated with the revolving movement of the plurality of compartments carried on common support-structure.

In a further embodiment, the combination includes the camera outer-support structure that supports the camera(s) being in the form of an outer-frame and/or outer-vessel shaped to receive and be mounted-about or on the liquid-containable inner-vessel in which the liquid media (normally water) is located, and into which (inner-vessel) the plurality of compartments are lowered and moved as above-described. The outer frame and/or outer-vessel is so-positioned and/or includes appropriate through-space window(s) therein that the compartment(s) is/are viewable by the camera(s) through the window(s), during surveillance of dissolution and/or disintegration of the tablets carried in the compartments.

In a further embodiment, the combination further includes the liquid-containable vessel itself, with the camera(s) being positioned and located such that above-noted surveillance and recording are possible, as the tablets are disintegrated and/or dissolved in the liquid media.

While it is within the scope of the invention for the camera(s) to be arranged and positioned to view downwardly into a liquid or even with water-tight lens positioned within the liquid-media within the tank or vessel containing the liquid media, in a preferred embodiment the liquid-containable vessel or waterbath preferably has at-least one or more of its sides transparent, such as glass or acrylic plastic, such that the camera(s) are located, positioned and mounted to view through the transparent wall(s), with the advantage that water reflections are avoided off-of the surface of the water (or other liquid) and such that the supporting structures for the plurality of compartments does not interfere with the lines of surveillance of the camera(s).

THE FIGURES

FIGS. 1 though 3 represent a common embodiment of the present invention. FIGS. 4 and 5 represent alternate embodiments.

FIG. 2 illustrates a top view of a part of the combination of FIG. 1, as taken along line 2—2 of FIG. 1, also diagrammatic in the illustration, with partial cut-away portraying the transparent wall of the liquid-containing inner vessel and portraying the window in the outer support plate through which the camera view the interior of the liquid-containing vessel.

FIG. 3 illustrates a side view of a part of the combination of FIG. 1, as taken along line 3—3 of FIG. 1, also diagrammatic in the illustration of the supporting plate having the camera mounted thereof.

FIG. 4 illustrates an embodiment basically the same as that of FIG. 2, except having a camera mounted on adjacent sides of the typically square structure as illustrated diagrammatically, such that at any one time, all of one side of a row of revolvable serially-arranged compartments are concurrently/simultaneously observable by at-least one of the cameras, viewed as a top view.

Figure 1:
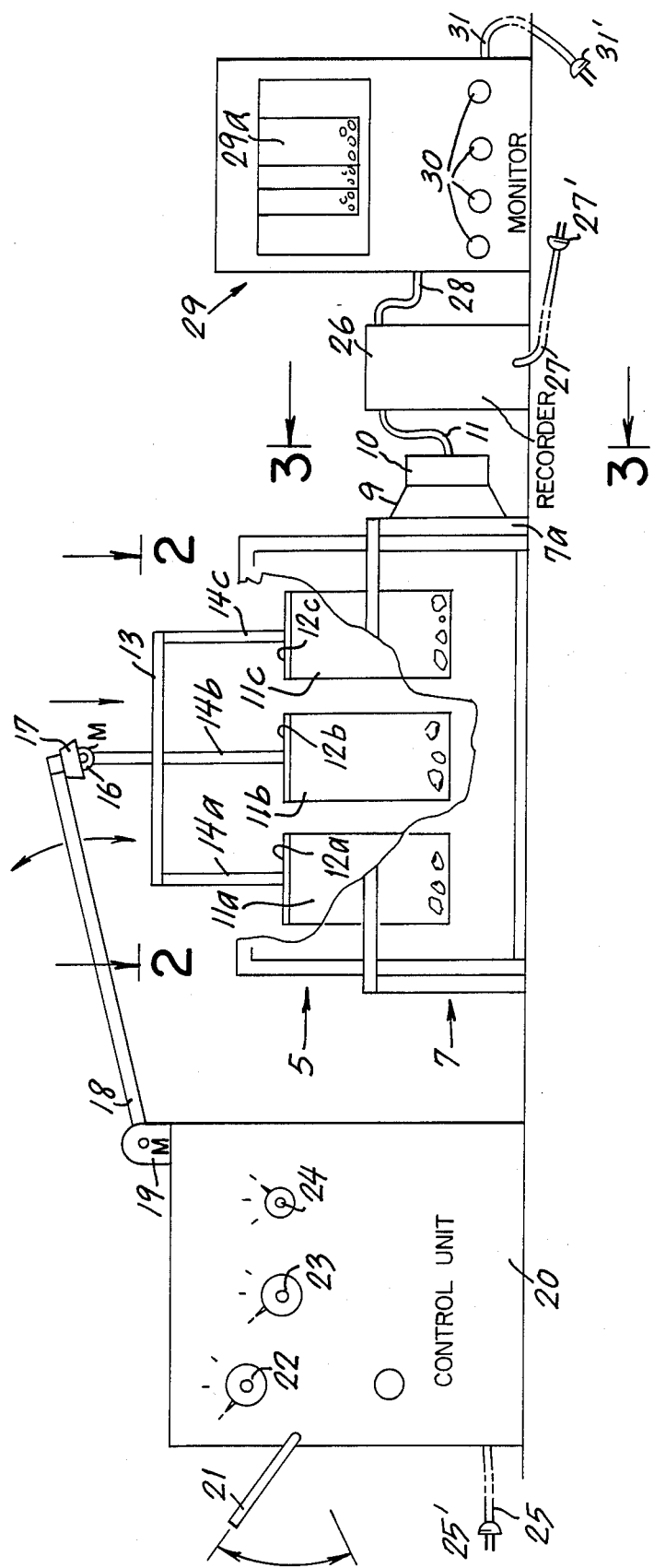
FIG. 1 illustrates an overall total preferred combination of the invention shown in-part diagrammatically as to state-of-the art components, and in greater detail as to particular novel aspects of other components of the total inventive combination, shown symbolically in side view of all components, arranged for functioning and for explaining the function(s) being achieved thereby.

FIG. 5 illustrates a further embodiment basically the same as that of FIG. 4, except that the second camera is mounted on a substantially opposite side substantially as shown, in order that for the one or more rows of compartments, at least one side of each is visible and observable at least one of the cameras, while in the preferred off-set arrangement illustrated, the second or back row is also partially visible and observable by a camera observing fully a first row, making all compartments observable simultaneously by a single camera by virtue of being off-set as illustrated.

DETAILED DESCRIPTION

In the figures as described below in greater detail, common elements are involved in different figures, and related indicia are utilized for identifying corresponding elements in the different figures and different embodiments, devoid of further description where not deemed necessary to a proper understanding.

As noted above, FIGS. 1 through 3 represent a common embodiment, and accordingly one or more of those Figures may be referred to in the description of that embodiment, as follow. The liquid or water containable open-top vessel 5 contains liquid-media, typically water contained within it. The frame structure 7 includes on the camera-face side of the vessel 5, a metal plate 7a that has a window 8 therein through which the interior liquid-media 6 is viewable by the electronic camera 10 having lens and camera support structure 9 adjoining and mounted suitably onto the face of the plate 7a. As shown in the cut-away, the window 8 may be seen, together with the metal 7a' of the metal plate 7a. The cord 11 represents diagrammatically the circuitries and wiring necessary of a conventional nature, feeding the electonic signals of viewed subject matter to the video recorder (such as typically a VCR/video cassette recorder) 26. The typically columnar tablet-support structures 11a, 11b and 11c each and all typically are cylindrical in shape, having transparent walls and an open top and a wire-mesh bottom in the typical prior-art fashion, having the mesh bottoms 30a, 30b, and 30c. The cylindrical vessels 11a, 11b and 11c each are supported by its individual horizontal support top-brace 12a, 12b and 12c. Each of the top-braces 12a, 12b and 12c are attached to a common horizontal brace 13 that is preferably rigidly, immovably attached to one or more downwardly-extending shafts such as shafts 14a, 14b and 14c mounted on or suspended from a revolving mechanism or motor 16 permanently mounted on the terminal or distal end of the support arm 18. The support arm 18 is movable upwardly and dowardwardly (and if desired, also laterally) by the drive motor 19 as controlled by conventional and prior art appropriate lever(s) 21, control knobs 22 and 23, and switch(s) 24 and the like, of the control unit 20, including circuitry and controls to the motor 17 above-noted. Power cords are typically and diagrammatically represented as 25, 27 and 31, and typical power plugs are typically and diagrammatically represented as 25', 27' and 31'. The recorded surveillance observations are typically played-back by existing prior art type vidoe-playback hardware, circuitry as above-noted represented as recorder 26—such as a VCR, through conventional prior art monitor cable(s) 27' into and through a typical prior art conventional or desired monitor 29 with its monitor-screen, having symbolic control knobs 30 and power cord (to the extent otherwise required) 31 with its symbolic plug 31'.

In FIG. 2, the symbolic direction of horizontal rotational movement is shown by arrows 32a and 32b.

FIG. 3 illustrates the face view of the support plate 7a (of support frame structure 7) and the camera 10 and its support structure 9 and cord 11, as viewed along lines 3—3 of FIG. 1.

FIG. 4 embodiment illustrates two separate cameras 10a and 10b, mounted separately on a support plates 7'a and 7"a by camera support structures 9a and 9b, for viewing through windows (not illustrated through the plates 7'a and 7"a, the same as illustrated by window 8 for plate 7a of FIG. 2. Symbolic direction of horozontal rotational movement is shown by arrows 32'a and 32'b. Accordingly, there is provided a camera for each of two adjacent sides of the squared vessel 5a.

FIG. 5 illustrates an alternate embodiment basically the same as that of FIG. 4, except that the second camera is mounted on an opposite mounting plate 7"b—of plates 7"a and 7"b, the cameras viewing through windows (not shown) which are the same as window 8 of FIG. 2. Additionally, this embodiment illustrates a preferred concept-embodiment of arranging the containers 11"a and 11"b in off-set rows (here, rows of three).

In each foregoing embodiments of this invention, the rotation by the rotary motor 16 is optional. Likewise, as noted-above the presence of the rotary motor 16 is preferred, but not essential to other aspects of the invention.

As previously noted, the monitor 29, its screen 29a and circuitry thereof, and the record playback mechanism of recorder 26 and circuitry thereof, jointly (or cummulatively) are adapted in conventional prior art mechanisms thereof, to project concurrently recording from both (or multiple) cameras such as from cameras 10a and 10b of FIG. 4 or cameras 10c and 10d of FIG. 5. Alternately, the units may be adapted to play-back separately or simultaneously on the same or different screens, in conventional prior art fashions making use of such conventional prior art mechanisms already a part of the state of the art.

It is within the scope and spirit of this invention, to make variations, modifications, and/or substitution of equivalents to extent that would be obvious to a person of ordinary skill in this art.

I claim:

1. A video device for pharmaceutical surveillance and recording timing of rates of disintegration or dissolving of pharmaceutical tablets, comprising in combination: (a) an electronic video camera means for powering movement of and for surveillance of tablets undergoing disintegration or dissolution of tablets in liquid media; (b) camera support means for supporting and positioning said electronic video camera means for observing tablets being disintegrated or dissolved in a liquid media; (c) timing means for indicating running or intermittent times during surveillance of said camera means; and (d) video recording means for recording observations made by said electronic video camera means and for recording said times associated with observations during powering and surveillance of said electronic video camera means.

2. A video device of claim 1, including a vessel containable of liquid and having side walls, at-least a portion of said side walls being sufficiently transparent such that disintegration or dissolution of tablet(s) within liquid media within said vessel is viewable by surveillance by said electronic video camera through said portion.

3. A video device of claim 1, including (e) tablet support and movement means for moving at least one tablet within liquid media sufficiently to cause the tablet(s) to disintegrate or dissolve over a period of time, and (f) vessel means for containing liquid media and for receiving said tablet support and movement means sufficiently into liquid media contained thereby, to make possible disintegration or dissolving of tablet(s) moved by said tablet support and movement means.

4. A video device of claim 3, in which said tablet support and movement means includes a plurality of separate compartments for segregating a plurality of at-least two tablets from one another while being moved within a liquid media, and in which said plurality are located and positioned relative to said electronic video camera means such that said plurality are substantially concurrently susceptible of surveillance thereof.

5. A video device of claim 4, in which said located and positioned plurality are arranged in side-by-side arrangement such that both are concurrently viewable by said electronic video camera means.

6. A video device of claim 4, in which said plurality includes at-least three of said separate compartments arranged in off-set staggered positions such that within predetermined minimum space all thereof are viewable by said electronic video camera substantially concurrently.

7. A video device of claim 4, in which said tablet support and movement means includes lateral movement means for intermittently moving different ones of said plurality to and from locations and positionings at which intermittently one or more of said plurality is susceptible of surveillance by said electonic video camera means.

8. A video device of claim 7, in which said tablet support and movement means is adapted to revolve said ' plurality.

9. A video device of claim 4, in which said camera support means includes support structure shaped to receive a waterbath-vessel containable of liquid media, such that said electronic video camera means is positioned to observe solid dosage forms by surveillance during disintegration or dissolution within liquid media placed within a waterbath-vessel.

10. A video device of claim 9, including said waterbath vessel.

11. A video device of claim 10, in which said vessel includes side walls, at-least a portion of said side walls being sufficiently transparent such that disintegration or dissolution of tablet(s) within liquid media within said vessel is viewable by surveillance by said electronic video camera through said portion.

12. A video device of one of claims 1 or 2 including a plurality of said electronic video camera means, said camera support means being additionally for supporting said plurality at different points of surveillance of tablets undergoing disintegration or dissolution in liquid media.

13. A video device of claims 1 or 2, including a plurality of said electronic video camera means, said camera support means being additionally for supporting said plurality at different points of surveillance of tablets undergoing disintegration or dissolution in liquid media.

14. A video device of one of claims 2 or 3 or 4 or 5 or 6 or 7 or 8 or 9 or 11 or 2 including a video monitor means for playback of recorded observations and recorded times from said video recording means, said video monitor means including video screen for displaying said recorded observations and recorded times, said video recording means additionally being for playing-back recorded observations and recorded times on said video screen.

15. A video device for pharmaceutical surveillance and recording timing of rates of disintegration or dissolving or pharmaceutical tablets, comprising in combination: (a) a plurality of electronic video camera means for powering movement of and for surveillance of tablets undergoing disintegration or dissolution of tablets in liquid media; (b) camera support means for supporting and positioning said electronic video camera means for observing tablets being disintegrated or dissolved in a liquid media and said camera support means being additionally for supporting said plurality at different points of surveillance of tablets undergoing disintegration or dissolution in liquid media; (c) timing means for indicating running or intermittent times during surveillance of said camera means; and (d) video recording means for recording observations made by said electronic video camera means and for recording said times associated with observations during powering and surveillance of said electronic video camera means.

16. A video device of claim 15, including a video monitor means for playback of recorded observations and recorded times from said video recording means, said video monitor means including at-least one video screen for displaying and recorded observations and recorded times, said video recording means additionally being for playing-back recorded observations and recorded times on said video screen.

17. A video device of claim 16, in which said video recording means and said video monitor means jointly are for simultaineously playing-back separately onto a divided screen, separate recorded observations and recorded times.

18. A video device for pharmaceutical surveillance and recording timing of rates of disintegration or dissolving of pharmaceutical tablets comprising in combination: an electronic video camera means for powering movement of and for surveillance of tablets undergoing disintegration or dissolution of tablets in liquid media; (b) camera support means for supporting and positioning said electronic video camera means for observing tablets being disintegrated or dissolved in liquid media; (c) timing means for indicating running or intermittent times during surveillance of said camera means; (d) video recording means for recording observations made by said electronic video camera means and for recording said times associated with observations during powering and surveillance of said electronic video camera means, and (e) a video monitor means for playback of recorded observations and recorded times from said video recording means, said video monitor means including a video screen for displaying said recorded observations and recorded times on said video screen.

19. A video device of claim 18, in which said video recording means and said video monitor means jointly are for simultaineously playing-back separately onto a divided screen, separte recorded observations and recorded times.

* * * * *